(12) United States Patent
Kobayashi et al.

(10) Patent No.: US 7,399,815 B2
(45) Date of Patent: Jul. 15, 2008

(54) FLUORINE-CONTAINING ALLYL ETHER COMPOUNDS, THEIR COPOLYMERS, AND RESIST COMPOSITIONS AND ANTI-REFLECTION FILM MATERIALS USING SUCH COPOLYMERS

(75) Inventors: Satoru Kobayashi, Saitama (JP);
Katsunori Kawamura, Saitama (JP);
Kazuhiro Yamanaka, Saitama (JP);
Haruhiko Komoriya, Saitama (JP);
Kazuhiko Maeda, Tokyo (JP)

(73) Assignee: Central Glass Company, Limited, Ube-shi (JP)

( * ) Notice: Subject to any disclaimer, the term of this patent is extended or adjusted under 35 U.S.C. 154(b) by 0 days.

(21) Appl. No.: 11/492,056

(22) Filed: Jul. 25, 2006

(65) Prior Publication Data

US 2006/0264592 A1    Nov. 23, 2006

Related U.S. Application Data

(62) Division of application No. 10/670,744, filed on Sep. 26, 2003, now Pat. No. 7,109,383.

(30) Foreign Application Priority Data

Sep. 27, 2002  (JP)  ............................. 2002-282543
Sep. 27, 2002  (JP)  ............................. 2002-282553

(51) Int. Cl.
*C08F 18/20*  (2006.01)

(52) U.S. Cl. .................. 526/246; 526/242; 526/245; 526/247; 430/270.1; 430/322; 430/326; 430/330; 430/907

(58) Field of Classification Search .................. None
See application file for complete search history.

(56) References Cited

U.S. PATENT DOCUMENTS 6,217,953 B1    4/2001   Heckmeier et al.
6,414,167 B1    7/2002   Miyazawa et al.
6,710,148 B2    3/2004   Harada et al.
7,060,771 B2    6/2006   Komoriya et al.
7,125,943 B2 *  10/2006  Sumida et al. .............. 526/308
2004/0106755 A1 6/2004   Sumida et al.
2006/0063902 A1 3/2006   Komoriya et al.

FOREIGN PATENT DOCUMENTS

| DE | 19945890 | 4/2000 |
| JP | 2002-80431 A | 3/2002 |
| JP | 2002-107938 A | 4/2002 |
| JP | 2002-201231 A | 7/2002 |
| JP | 2002-234916 A | 8/2002 |
| JP | 2002-249520 A | 9/2002 |
| WO | WO 02/06901 A2 | 1/2002 |
| WO | WO 03061698 | 7/2003 |

OTHER PUBLICATIONS

Kamon et al., "Newly Developed Acrylic Copolymers for ArF Photoresist," *Journal of Photopolymer Science and Technology*, vol. 18, No. 4 (2002), pp. 535-540.

* cited by examiner

*Primary Examiner*—Rosalynd Keys
(74) *Attorney, Agent, or Firm*—Crowell & Moring LLP

(57) ABSTRACT

The invention relates to a fluorine-containing allyl ether compound represented by the formula 1,

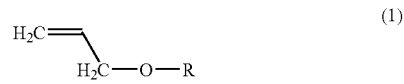

(1)

wherein R represents an organic group containing at least one fluorine atom and an alicyclic structure. The invention further relates to a fluorine-containing copolymer containing a first unit derived from the fluorine-containing allyl ether represented by the formula 1; and a second unit derived from a vinyl monomer.

7 Claims, No Drawings

FLUORINE-CONTAINING ALLYL ETHER COMPOUNDS, THEIR COPOLYMERS, AND RESIST COMPOSITIONS AND ANTI-REFLECTION FILM MATERIALS USING SUCH COPOLYMERS

CROSS REFERENCE TO RELATED APPLICATION

The present application is a division of application Ser. No. 10/670,744, filed Sep. 26, 2003, which claims benefit to Japanese priority application nos. 2002-282543, filed Sep. 27, 2002, and 2002-282553, filed Sep. 27, 2002, whose disclosure is hereby incorporated by reference in its entirety into the present application.

BACKGROUND OF THE INVENTION

The present invention relates to (a) fluorine-containing allyl ether compounds, which are useful as raw material monomers for producing polymers, (b) fluorine-containing copolymers of the ally ether compounds, and (c) resist compositions and anti-reflection film materials using the fluorine-containing copolymers.

In recent years, as demands for finer semiconductors have been increasing, there have been conducting active developments of next generation lithography technology using shorter wavelength light sources (see Y. Kamon et al., *J. Photopolym. Sci. Technol.*, 15, 535 (2002)). In such developments, the resist composition development has been holding an important position. Now, a major resist type is a positive-type resist composition, in which an acid is generated by light irradiation and then solubility of a resin of the resist composition in alkali aqueous solution changes due to a chemical change of the resin by an action of the acid as catalyst. In the trend toward shorter wavelength light source, there are problems that resins (e.g., novolak resins, acrylic resins and styrene resins) used in current resists are insufficient in transparency.

SUMMARY OF THE INVENTION

It is therefore an object of the present invention to provide a monomer that can be a raw material for producing base polymers, which are low in light scattering and absorption and high in transparency, for resist compositions and optical materials.

It is another object of the present invention to provide a fluorine-containing copolymer that is low in light scattering and absorption and high in transparency and that is useful for producing resist compositions and anti-reflection materials.

It is still another object of the present invention to provide a resist composition or anti-reflection film material using the fluorine-containing copolymer.

According to a first aspect of the present invention, there is provided a fluorine-containing allyl ether compound represented by the formula 1,

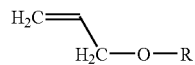

(1)

wherein R represents an organic group comprising at least one fluorine atom and an alicyclic structure.

According to a second aspect of the present invention, there is provided a fluorine-containing copolymer comprising:

a first unit derived from the fluorine-containing allyl ether represented by the formula 1; and a second unit derived from a vinyl monomer.

According to the second aspect of the present invention, there are provided a resist composition and an anti-reflection material, each comprising the fluorine-containing copolymer.

DESCRIPTION OF THE PREFERRED EMBODIMENTS

Acrylic resins and styrene resins that have been used in the past for resist compositions are low in transparency for ultraviolet rays (particularly light rays of vacuum ultraviolet region), since, for example, these resins are high in light absorption due to structures such as carbonyl group and aromatic ring. In contrast, the present inventors unexpectedly found the above novel fluorine-containing allyl ether (represented by the formula 1), which is useful as a raw material monomer of highly transparent fluorine-containing copolymers. Furthermore, we unexpectedly found the above novel fluorine-containing copolymer, which is high in transparency and can be obtained by copolymerizing the fluorine-containing allyl ether with a vinyl monomer. This vinyl monomer can be selected from α-trifluoromethyl acrylic esters and acrylic esters, which are monomers useful for resist resins. Furthermore, the fluorine-containing copolymer is soluble in various organic solvents and therefore suitable for coating use. The fluorine-containing copolymer may contain a third unit derived from a monomer containing a norbornene structure.

As stated above, R of the formula 1 represents an organic group comprising at least one fluorine atom and an alicyclic structure. Examples of this organic group include cycloalkyl groups, heterocyclic groups, cyclodienyl groups, and heterocyclic groups each containing at least one heteroatom such as nitrogen, oxygen and sulfur. The alicyclic structure may be partially replaced with a first alkyl group containing an unsaturated bond, oxygen or the like or with a second alkyl group containing none of these. The alicyclic structure may be a single ring structure (e.g., cyclohexyl and lactone ring) or a multi-ring structure derived from bicyclo[2.2.1]heptane, tricyclo[5.2.1.0$^{2.6}$]-decane, tetracyclo[4.4.0.1$^{2.5}$.1$^{7.10}$]dodecane or adamantane. Furthermore, the alicyclic structure may contain, for example, a reactive group that is released by the action of an acid. Specific examples of the organic group are those represented by the following structural formulas.

In the following formulas, $R^1$ is H or a $C_1$-$C_6$ alkyl group and optionally contains a heteroatom(s) such as oxygen; $R^2$ is a $C_0$-$C_5$ alkyl group; $R^3$ is H or F; $R^4$ is $CF_3$, OH, $CO_2H$, $CO_2R^5$, or $OCOR^5$ where $R^5$ is a $C_1$-$C_6$ alkyl group; $R^6$ is H or F; and $R^7$ is H or $C_1$-$C_5$ alkyl group.

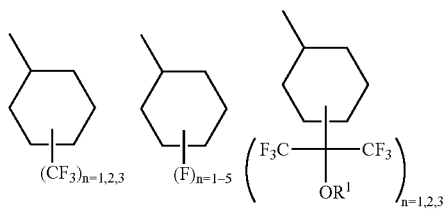

-continued

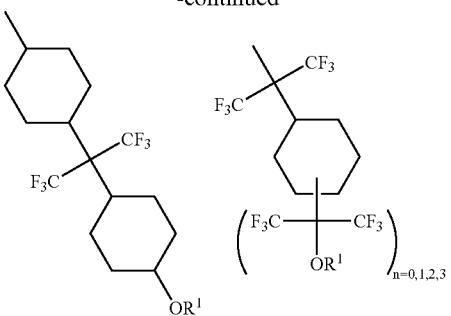

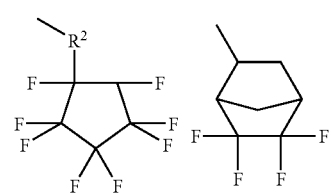

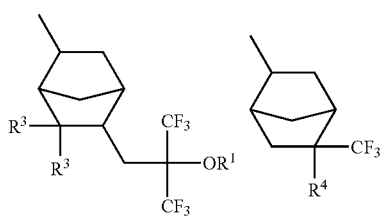

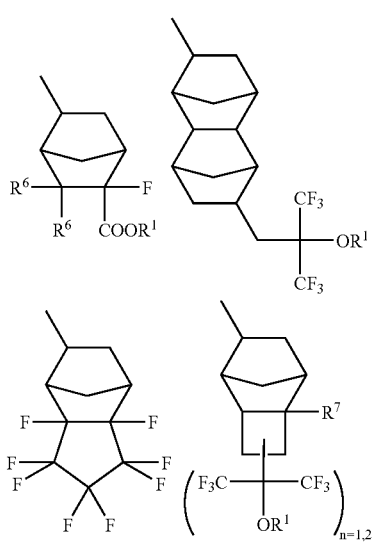

Of the allyl ethers containing organic groups represented by the above structural formulas, those containing structures, such as cyclohexane, bicyclo[2.2.1]heptane and norbornane, in their alicyclic structures are preferable as monomers for producing resist compositions, since polymers derived from those allyl ethers are low in light absorption caused by double bond and are superior in heat resistance. A hexafluoroisopropanol unit (—C(CF$_3$)$_2$—OH) or hexafluoroisopropanol derivative unit (—C(CF$_3$)$_2$—OR$^1$, where R$^1$ is a hydrogen or alkyl group having a carbon atom number of from 1 to 6 and may contain a hetero atom(s) such as oxygen), which is represented by the following formula 2, serves to improve adhesion of the resulting polymer to substrate.

It is possible to apply various known processes to produce the fluorine-containing allyl ether of the present invention. For example, it is possible to apply Williamson reaction to treat a fluorine-containing alcohol with an alkali metal, followed by a reaction with an allyl halide. As this alkali metal, it is possible to use various alkali metal compounds, such as sodium hydride, potassium hydride, sodium hydroxide, and potassium hydroxide. For example, the allyl halide may be selected from allyl fluoride, allyl chloride, allyl bromide, and allyl iodide. Of these, allyl chloride, allyl bromide and allyl iodide are preferable, since they are good in reactivity to efficiently obtain the target allyl ether.

It is possible to use a reaction solvent in the process for producing the allyl ether. This solvent is not particularly limited, as long as it does not interfere with the target reaction of the process. It is preferable to use a reaction solvent (e.g., tetrahydrofuran, diethyl ether, and dimethylformamide) that is low in reactivity with the alkali metal compound. Although the reaction temperature is not particularly limited, it is preferably in a range of −30° C. to +100° C., more preferably in a range of −10° C. to +80° C., in view of reaction and handling easiness. The reaction product can be separated and purified by a common process, such as concentration, extraction, distillation, recrystallization, filtration, column chromatography, and combinations of these.

As explained in detail hereinafter, the fluorine-containing allyl ether of the present invention can be copolymerized with a monomer (e.g., α-trifluoromethyl acrylic esters and acrylic esters) that is useful for resist resins. The resulting fluorine-containing copolymers are soluble in various organic solvents and therefore are suitable for the coating use. Specifically, the allyl ether is useful as a raw material monomer for base polymers of resists that are low in light scattering and absorption, for producing semiconductors. Furthermore, the allyl ether is useful as a monomer for base polymers of plastic optical fibers, optical waveguide materials, and optical materials such as anti-reflection film materials.

The vinyl monomer used in the present invention provides the fluorine-containing copolymer with a suitable molecular weight in practical use and makes sure of the effect of high transparency caused by the allyl ether. The vinyl monomer is not particularly limited, and it can be selected from common vinyl monomers. Its examples include α-olefins (e.g., ethylene, propylene), cyclic olefins (e.g., norbornene and cyclohexene), vinyl ether, vinyl ester, acrylic acid, methacrylic acid, acrylic ester, methacrylic ester, styrene, vinyl sulfonic acid, vinyl silane, and anhydrous maleic acid. The vinyl monomer may contain at least one selected from fluorine atoms, heteroatoms (e.g., oxygen), functional groups, cyclic structure organic groups (e.g., adamantyl group), and reactive groups that are released by the action of acid. Furthermore, it is possible to use tetrafluoroethylene, chlorotrifluoroethylene, hexafluoroisobutene, hexafluoropropylene, trifluoroethylene, perfluorovinyl ether, and fluoroolefins such as olefins represented by the following formula 3.

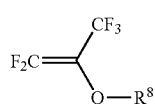
(3)

wherein $R^8$ represents an alkyl group having a carbon atom number of from 1 to 15 and may contain a heteroatom(s) such as oxygen.

Of examples of the vinyl monomer, α-trifluoromethyl acrylic ester and acrylic ester are preferable since they are superior in copolymerizability with the fluorine-containing allyl ether. Examples of the organic group of the ester moiety in α-trifluoromethyl acrylic ester or acrylic ester are straight-chain, branched and cyclic alkyl groups such as methyl group, ethyl group, isopropyl group, t-butyl group, and adamantyl group. Such organic group may contain a heteroatom(s) (e.g., oxygen) and/or a fluorine atom(s). Furthermore, it may contain a reactive group that is released by the action of acid.

In the preparation of the fluorine-containing copolymer, it may be optional to use another monomer in addition to the fluorine-containing allyl ether and the vinyl monomer, as long as it does not interfere with transparency of the fluorine-containing copolymer. Examples of such another monomer include α-olefins (e.g., ethylene, propylene), cyclic olefins (e.g., norbornene and cyclohexene), vinyl ether, vinyl ester, acrylic acid, methacrylic acid, acrylic ester, methacrylic ester, allyl ether that is different from the fluorine-containing allyl ether of the present invention, styrene, vinyl silane, and anhydrous maleic acid. The another monomer may contain at least one selected from fluorine atoms, heteroatoms (e.g., oxygen), functional groups, cyclic structure organic groups (e.g., adamantyl group), and reactive groups that are released by the action of acid. Furthermore, it is possible to use tetrafluoroethylene, chlorotrifluoroethylene, hexafluoroisobutene, hexafluoropropylene, trifluoroethylene, perfluorovinyl ether, and fluoroolefins such as olefins represented by the above formula 3. Of the above examples of the another monomer, norbornene, anhydrous maleic acid and monomers containing alicyclic structures (e.g., adamantyl group) are preferable, since they can improve the fluorine-containing copolymer as a resist composition in etching resistance. The above-mentioned examples of the another monomer can be used alone or in combination.

The ratio of the fluorine-containing allyl ether to the vinyl monomer in the preparation of the fluorine-containing copolymer is not particularly limited. The fluorine-containing copolymer contains each of the units derived from the fluorine-containing allyl ether and the vinyl monomer in an amount of preferably 0.1 mol % or greater, more preferably 1 mol % or greater, in order to improve the fluorine-containing copolymer in transparency.

The number average molecular weight of the fluorine-containing copolymer may be from 1,000 to 1,000,000, preferably from 2,000 to 100,000. If it is too small, the fluorine-containing copolymer may become insufficient in strength and inferior in heat resistance in the use as a resist composition. If it is greater than 100,000, it may become inferior in solubility in solvent.

The process for producing the fluorine-containing copolymer is not particularly limited. It can be a known polymerization such as anionic polymerization, radical polymerization, ion polymerization or coordination polymerization. Of these, radical polymerization is preferably used. The polymerization can be conducted by a known manner such as bulk polymerization, solution polymerization, suspension polymerization or emulsion polymerization.

The temperature for conducting the polymerization can be suitably set depending on the polymerization process, polymerization manner and the type of the polymerization initiator. It may be 20-200° C., preferably 40-120° C.

The radical polymerization initiator for conducting the radical polymerization is not particularly limited. Its examples include azo compounds, peroxides and redox compounds.

It is optional to use a polymerization solvent in the polymerization for producing the fluorine-containing copolymer. Although the polymerization solvent is not particularly limited, it is preferably one that does not greatly interfere with the polymerization. Its typical examples are ketones such as acetone; aromatic solvents such as toluene; cyclic hydrocarbon solvents such as cyclohexane; alcohols such as isopropyl alcohol; and esters such as butyl acetate. Furthermore, it is possible to use a molecular weight adjusting agent, such as mercaptan, in the polymerization.

The polymerization may be conducted by radical emulsion polymerization, as stated above, using an emulsifying agent. This emulsifying agent may be an anion and/or nonion emulsifying agent. The radical polymerization initiator usable in the emulsion polymerization is not limited to a particular type. A water-soluble initiator such as persulfate is preferably used.

The suspension stabilizer for conducting suspension polymerization is not particularly limited. It is possible to use a water soluble polymer such as methyl cellulose.

The fluorine-containing copolymer of the present invention is useful as resist compositions for producing semiconductors and as anti-reflection film materials. Furthermore, it is useful as core materials, cladding materials, covering materials, and optical bonds for resin optical fibers and optical waveguides.

The use of the fluorine-containing copolymer is not particularly limited in the resist uses. For example, it can be used as a polymer that changes solubility in alkali aqueous solution by the generation of acid. Such polymer can be prepared by introducing an acid-labile protecting group into at least one of the fluorine-containing allyl ether, the vinyl monomer, and the another monomer.

For example, it is possible to prepare a resist by using an organic solvent, a photoacid generator, and an additive(s), in addition to the fluorine-containing copolymer. Furthermore, it is optional to add another polymer to prepare a resin blend resist.

The fluorine-containing copolymer according to the present invention may be formed into a film by dissolving the copolymer in a solvent to prepare a coating solution and then by applying the coating solution to a substrate. This solvent is not particularly limited as long as the polymer can be dissolved therein. Its examples include ketones such as acetone and methyl ethyl ketone; polyhydric alcohols and their derivatives such as ethylene glycol monoacetate, propylene glycol, propylene glycol monoacetate, and propylene glycol monomethyl ether acetate; ethers such as tetrahydrofuran and dioxane; esters such as ethyl acetate, butyl acetate, methyl lactate, and ethyl lactate; aromatic solvents such as xylene and toluene; and fluorine-containing solvents such as fleon. The solvent for preparing the coating solution may be a single solvent or a mixture of at least two solvents.

The above-mentioned photoacid generator for a resist composition is not particularly limited. It can be suitably selected from acid generators for chemically amplified resists. Examples of such acid generators are bissulfonyldiazomethanes, nitrobenzyl derivatives, onium salts, halogen-containing triazine compounds, cyano group-containing oximesulfonate compounds, and other oximsulfonate compounds. The acid generator may be used in the form of a single compound or a mixture of at least two compounds. The content of the acid generator in the resist composition may be 0.5-20 parts by weight, relative to 100 parts by weight of the copolymer.

According to need, it is optional to add an additive to the copolymer. Examples of such additive are solubility inhibitor, plasticizer, stabilizer, coloring agent, light amplifier, surfactant, tackifier, leveling agent, deforming agent, adhesion enhancing agent, and quencher.

The above-mentioned resist composition according to the present invention can be used in conventional resist patterning methods, as exemplified in the following. Firstly, a solution of the resist composition is applied to a supporting member (e.g., silicon wafer) by spin coating, followed by drying to form a photosensitive layer. Then, the photosensitive layer is exposed to a light from an exposure apparatus through a mask pattern, followed by heating. Then, a development treatment is conducted by using an alkali aqueous solution, thereby obtaining a resist pattern conforming to the mask pattern.

It is possible to apply a solution of the fluorine-containing copolymer to substrate, followed by drying and according to need heating, in order to form an anti-reflection film having a thickness for showing anti-reflection.

The following nonlimitative examples are illustrative of the present invention. Examples 1 to 2 and Examples 3 to 8 are respectively illustrative of the first and second aspects of the present invention.

EXAMPLE 1

Synthesis of Allyl Ether 1

A 300 mL glass container was charged with 29.2 g of an alcohol 1 represented by the following formula, 14.5 g of allyl bromide, and 100 mL of dry dimethylformamide. While the resulting mixture was stirred under cooling in a water bath, the inside atmosphere of the container was replaced with nitrogen. Then, 6.0 g of 60% sodium hydride were gradually added to the container under nitrogen stream. After stirring for 30 min, 30 cc of water were gradually added to the container, and the reaction was terminated. The resulting reaction mixture liquid was extracted with diethyl ether to isolate an organic matter, followed by washing with saturated brine, drying with anhydrous magnesium sulfate, distilling the solvent off, and distillation under reduced pressure, thereby obtaining 30.2 g of the target compound, an allyl ether 1 represented by the following formula.

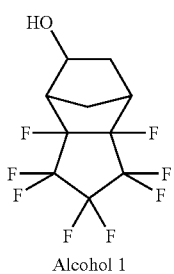

Alcohol 1

-continued

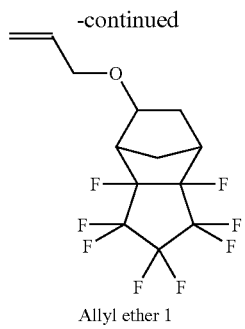

Allyl ether 1

The ally ether 1 was a mixture of two kinds of stereoisomers. The obtained compound was identified by nuclear magnetic resonance and mass spectroscopy. The obtained data are as follows.

$^1$H NMR (CDCl$_3$, standard: TMS, 400 MHz) δ 1.6-1.7 (m, 2H), 2.0-2.4 (m, 2H), 2.8-3.0 (m, 2H), 3.8-4.0 (m, 3H), 5.2-5.3 (m, 2H), 5.8-5.9 (m, 1H) MS m/z (%) 322 (M+, 100), 239 (36), 95 (45).

EXAMPLE 2

Synthesis of Allyl Ether 2

Example 1 was repeated except in that 29.2 g of the alcohol 1 were replaced with 41.6 g of an alcohol 2 represented by the following formula, thereby obtaining 18.2 g of the target compound, an allyl ether 2 represented by the following formula.

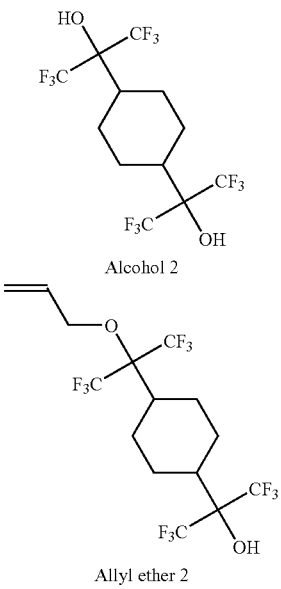

The obtained identification data are as follows.

$^1$H NMR (CDCl$_3$, standard: TMS, 400 MHz) δ 1.6-1.7 (m, 4H), 2.0-2.1 (m, 4H), 2.2-2.3 (m, 2H), 2.94 (s, 1H), 4.27 (d, J=5.2 Hz, 2H), 5.22 (dd, J=1.2, 10.4 Hz), 5.31 (dd, J=1.2, 17.0 Hz, 1H), 5.8-5.9 (m, 1H) MS m/z (%) 456 (M+, 1), 249 (100), 207 (47).

EXAMPLE 3

A 50 mL pressure-proof container was charged with 8.05 g of the allyl ether 1 of Example 1, 4.90 g of α-trifluoromethylacrylic t-butyl ester (hereinafter TFMA-B), 0.17 g of di-t-butylperoxypivalate, and 2.60 g of butyl acetate. While the resulting mixture was stirred, the inside atmosphere of the container was replaced with nitrogen. Then, the reaction was conducted, while the container was maintained at 60° C. for 20 hr. After the reaction, 3 g of butyl acetate were added to the cooled reaction liquid to have a homogeneous solution. A polymer was reprecipitated using 1 L of n-hexane, followed by filtration and vacuum drying, thereby obtaining 6.20 g of a white polymer. The obtained polymer was found by gel permeation chromatography (GPC) using polystyrene as a standard to have a weight average molecular weight of 11,000. The polymer was found by $^{19}$F NMR peak strength to contain 44 mol % of a unit derived from the allyl ether 1 and 56 mol % of a unit derived from the TFMA-B. The polymer was soluble in propylene glycol monomethylacetate. The resulting solution was applied to a substrate to form a film of 100 nm thickness, and this film was found to have a light transmittance of 98% at 193 nm wavelength.

EXAMPLE 4

A 50 mL pressure-proof container was charged with 4.19 g of the allyl ether 1, 7.06 g of α-trifluoromethylacrylic 2-methyl-2-adamantyl ester (hereinafter TFMA-MAD), 3.43 g of 3-(5-bicyclo[2.2.1]heptane-2-yl)-1,1,1-trifluoro-2-(trifluoromethyl)propane-2-ol (hereinafter BTHB-NB), 0.17 g of di-t-butylperoxypivalate, and 2.94 g of butyl acetate. Then, the same steps as those of Example 3 were conducted except in that 1 L n-hexane were replaced with 1 L of a mixture or methanol and water (methanol:water=1:1 in volume). Thereby, 8.70 g of a white polymer were obtained. The weight average molecular weight of the polymer was 7,300. The obtained polymer was found to contain 29 mol % of a unit derived from the allyl ether 1, 55 mol % of a unit derived from TFMA-MAD, and 16 mol % of a unit derived from BTHB-NB. The film (thickness: 100 nm) was found to have a light transmittance of 99% at 193 nm wavelength.

EXAMPLE 5

A 50 mL pressure-proof container was charged with 4.56 g of the allyl ether 2 of Example 2, 4.90 g of TFMA-B, 4.11 g of BTHB-NB, 0.25 g of α,α'-azobisisobutyronitrile, and 2.71 g of butyl acetate. Then, the same steps as those of Example 4 were conducted, except in that the container was maintained at 70° C. for 20 hr to conduct the reaction, thereby obtaining 6.60 g of a white polymer. The weight average molecular weight of the polymer was 11,000. The obtained polymer was found to contain 23 mol % of a unit derived from the allyl ether 2, 52 mol % of a unit derived from TFMA-B, and 25 mol % of a unit derived from BTHB-NB. The film (thickness: 100 nm) was found to have a light transmittance of 99% at 193 nm wavelength.

EXAMPLE 6

A 50 mL pressure-proof container was charged with 6.44 g of the allyl ether 1, 3.33 g of hexafluoro-2-propyl acrylate (hereinafter HFIP-A), 3.51 g of methacrylic acid 2-methyl-2-adamantyl ester (hereinafter MA-MAD), 0.17 g of di-t-butylperoxypivalate, and 2.66 g of butyl acetate. Then, the same steps as those of Example 3 were conducted, thereby obtaining 8.60 g of a white polymer. The weight average molecular weight of the polymer was 18,000. The obtained polymer was found by $^{19}$F NMR peak strength and thermogravimetry to contain 24 mol % of a unit derived from the allyl ether 1, 40 mol % of a unit derived from HFIP-A, and 36 mol % of a unit derived from MA-MAD. The film (thickness: 100 nm) was found to have a light transmittance of 96% at 193 nm wavelength.

EXAMPLE 7

The polymer obtained in Example 4 was dissolved in propylene glycol monomethyl ether acetate to have a solid matter concentration of 10 wt %. Then, an acid generator, triphenylsulfonium triflate made by Midori Kagaku Co., Ltd., was dissolved in an amount of 2 parts by weight per 100 parts by weight of the polymer, followed by filtration with 0.2 μm membrane filter, thereby preparing a resist solution. This resist solution was applied to a silicon wafer by spin coating to form a resist film having a thickness of 500 nm. Then, the resist film was subjected to a preliminary baking at 110° C., followed by exposure at 248 nm using a KrF excimer laser and then by a post exposure baking at 120° C. Then, the resist film was developed by a puddle development at 23° C. for 1 minute using 2.38 wt % tetramethylammonium hydroxide aqueous solution, followed by washing with pure water and drying. As a result, the non-exposed portion was not dissolved by the tetramethylammonium hydroxide aqueous solution, but the laser exposed portion was completely dissolved thereby. In other words, the resist film was found to have a necessary positive-type resist behavior.

EXAMPLE 8

The polymer obtained in Example 3 was dissolved in propylene glycol monomethyl ether acetate to have a solid matter concentration of 30 wt %. The resulting coating solution was applied to a glass substrate by spin coating to form a film having a thickness of 100 nm. Then, the film was subjected to a baking at 110° C. The resulting coated glass substrate was found to have a reflectance of 2.0%.

The entire disclosure of each of Japanese Patent Application Nos. 2002-282543 filed on Sep. 27, 2002 and 2002-282553 filed on Sep. 27, 2002, including specification, claims, summary and drawings, is incorporated herein by reference in its entirety.

What is claimed is:

1. A fluorine-containing copolymer comprising:
   a first unit derived from a fluorine-containing allyl ether represented by the formula 1; and
   a second unit derived from a vinyl monomer,

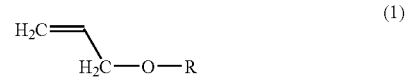

(1)

wherein R represents an organic group comprising at least one fluorine atom and an alicyclic structure.

2. A fluorine-containing copolymer according to claim 1, wherein the vinyl monomer is an α-trifluoromethyl acrylic ester.

3. A fluorine-containing copolymer according to claim 1, wherein the vinyl monomer is an acrylic ester.

4. A fluorine-containing copolymer according to claim 1, further comprising a third unit derived from a monomer containing a norbornene structure.

5. A fluorine-containing copolymer according to claim 1, wherein the organic group R is represented by one of the following formulas,

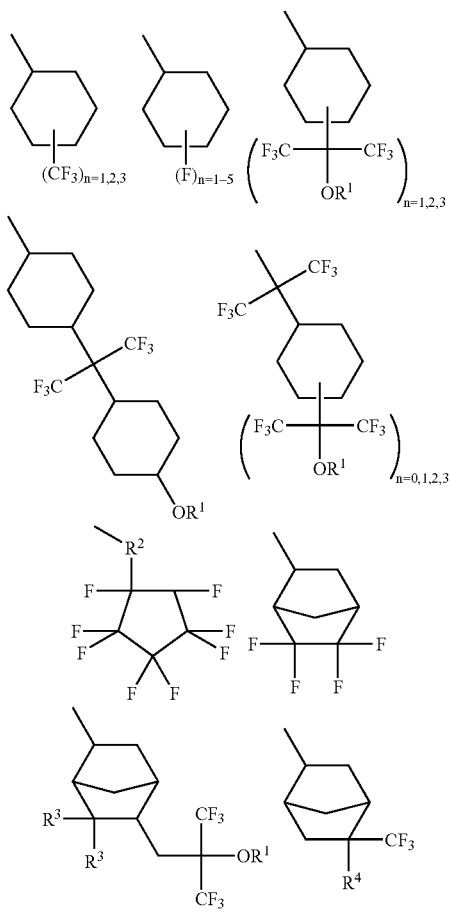

-continued

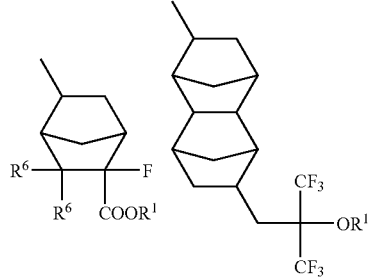

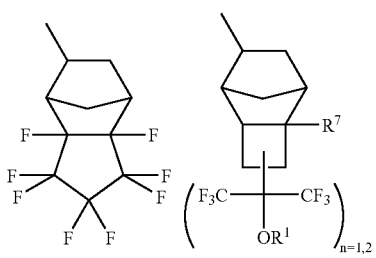

wherein $R^1$ is H or a $C_1$-$C_6$ alkyl group and optionally contains a heteroatom;

$R^2$ is a $C_0$-$C_5$ alkyl group;

$R^3$ is H or F; $R^4$ is $CF_3$, OH, $CO_2H$, $CO_2R^5$, or $OCOR^5$ where $R^5$ is a $C_1$-$C_6$ alkyl group;

$R^6$ is H or F; and $R^7$ is H or $C_1$-$C_5$ alkyl group.

6. A resist composition comprising a fluorine-containing copolymer according to claim 1.

7. An anti-reflection film material comprising a fluorine-containing copolymer according to claim 1.

* * * * *